(12) United States Patent
Styrc et al.

(10) Patent No.: US 9,408,693 B2
(45) Date of Patent: Aug. 9, 2016

(54) KIT WHICH IS INTENDED TO BE IMPLANTED IN A BLOOD VESSEL, AND ASSOCIATED TUBULAR ENDOPROSTHESIS

(75) Inventors: Mikolaj Witold Styrc, Kopstal (LU); Eric Perouse, Paris (FR)

(73) Assignee: CORMOVE, Bornel (FR)

( * ) Notice: Subject to any disclaimer, the term of this patent is extended or adjusted under 35 U.S.C. 154(b) by 1534 days.

(21) Appl. No.: 11/887,839

(22) PCT Filed: Mar. 24, 2006

(86) PCT No.: PCT/FR2006/000660
§ 371 (c)(1),
(2), (4) Date: Oct. 4, 2007

(87) PCT Pub. No.: WO2006/106205

PCT Pub. Date: Oct. 12, 2006

(65) Prior Publication Data

US 2009/0012600 A1    Jan. 8, 2009

(30) Foreign Application Priority Data

Apr. 5, 2005    (FR) .................................. 05 03374

(51) Int. Cl.
*A61F 2/24*    (2006.01)

(52) U.S. Cl.
CPC ............... *A61F 2/2418* (2013.01); *A61F 2/24* (2013.01); *A61F 2/2412* (2013.01); *A61F 2/2475* (2013.01); *A61F 2210/0014* (2013.01); *A61F 2220/0025* (2013.01); *A61F 2250/006* (2013.01); *A61F 2250/0039* (2013.01); *A61F 2250/0098* (2013.01)

(58) Field of Classification Search
USPC ............... 623/1.24, 1.26, 2.1–2.19, 1.3, 1.31
See application file for complete search history.

(56) References Cited

U.S. PATENT DOCUMENTS

| 4,705,516 A | * | 11/1987 | Barone et al. ............... 623/2.39 |
| 6,425,916 B1 | * | 7/2002 | Garrison et al. ............ 623/2.11 |
| 2002/0032481 A1 | | 3/2002 | Gabbay |
| 2002/0099439 A1 | * | 7/2002 | Schwartz et al. ............ 623/1.24 |

(Continued)

FOREIGN PATENT DOCUMENTS

| EP | 0 850 607 | 7/1998 |
| FR | 2 847 800 | 6/2004 |

(Continued)

OTHER PUBLICATIONS

International Search Report issued Oct. 17, 2006 in the International (PCT) Application of which the present application is the U.S. National Stage.

*Primary Examiner* — Yashita Sharma
*Assistant Examiner* — Rebecca Preston
(74) *Attorney, Agent, or Firm* — Wenderoth, Lind & Ponack, L.L.P.

(57) ABSTRACT

The invention relates to a kit including a tubular endoprosthesis having an inner surface delimiting a channel with a longitudinal axis. The kit includes a prosthetic valve designed to be implanted in the channel. The valve includes a supporting frame having an outer surface designed to be pressed against the inner surface, and a flexible cover connected to the frame. The inner surface has at least two segments with variable cross-section along the longitudinal axis. The segments form respectively a proximal stop and a distal stop to lock the axial displacement of the outer surface along the inner surface along two opposite directions.

7 Claims, 2 Drawing Sheets

(56) References Cited

U.S. PATENT DOCUMENTS

| | | |
|---|---|---|
| 2002/0151970 A1 | 10/2002 | Garrison et al. |
| 2002/0188348 A1* | 12/2002 | DiMatteo ............. A61F 2/2412 623/1.24 |
| 2003/0040792 A1* | 2/2003 | Gabbay ........................ 623/2.11 |
| 2003/0149477 A1 | 8/2003 | Gabbay |
| 2004/0106977 A1* | 6/2004 | Sullivan et al. ............. 623/1.12 |
| 2004/0210249 A1* | 10/2004 | Fogarty ............ A61B 17/12022 606/200 |
| 2004/0210305 A1* | 10/2004 | Shu et al. ..................... 623/2.11 |
| 2005/0096735 A1* | 5/2005 | Hojeibane et al. ........... 623/1.24 |
| 2005/0137691 A1* | 6/2005 | Salahieh et al. ............. 623/2.11 |
| 2005/0137694 A1* | 6/2005 | Haug .................... A61F 2/2418 623/2.11 |
| 2005/0203614 A1* | 9/2005 | Forster .................. A61F 2/2418 623/2.11 |
| 2005/0283225 A1* | 12/2005 | Klisch ......................... 623/1.15 |

FOREIGN PATENT DOCUMENTS

| | | |
|---|---|---|
| WO | 91/17720 | 11/1991 |
| WO | 00/47139 | 8/2000 |
| WO | 01/56512 | 8/2001 |
| WO | 02/22054 | 3/2002 |

\* cited by examiner

KIT WHICH IS INTENDED TO BE IMPLANTED IN A BLOOD VESSEL, AND ASSOCIATED TUBULAR ENDOPROSTHESIS

BACKGROUND OF THE INVENTION

I. Technical Field

The present invention relates to a kit which is intended to be implanted in a blood vessel, of the type comprising a tubular endoprosthesis which has an inner surface which delimits a channel having a longitudinal axis; and a prosthetic valve which is intended to be implanted in the channel, the valve comprising a carrier reinforcement which has an outer surface which is intended to be pressed against the inner surface of the endoprosthesis, the reinforcement being able to be deformed radially from a folded position for placement to a deployed position for implantation; a flexible shutter which is connected to the reinforcement and which can be deformed between a blocking position in which it is extended transversely and a release position in which it is contracted transversely under the action of the flow moving in the channel.

II. Description of Related Art

From EP-A-0 850 607, a kit of the above-mentioned type is known which comprises a tubular endoprosthesis and a prosthetic valve which has a deformable carrier reinforcement and a flexible shutter which is fixed to the reinforcement.

A kit of this type is intended to be implanted in place of a valve in a blood vessel.

Valves of this type are, for example, present in the heart, between the auricles and the ventricles, or at the outlet of the right ventricle and the left ventricle. These valves ensure one-way circulation of the blood flow, preventing blood reflux following the ventricular contraction.

In order to carry out a valve replacement, the tubular endoprosthesis provided in the kit is implanted in the portion of the vessel in which the defective valve is located. Then, the prosthetic valve in the folded state thereof is moved into the inner channel delimited by the endoprosthesis and is pressed against this endoprosthesis by inflating a balloon.

A device of this type is not entirely satisfactory. The relative positioning of the prosthetic valve relative to the endoprosthesis is approximate and the fixing of the valve in the endoprosthesis is not very secure.

SUMMARY OF THE INVENTION

An object of the invention is therefore to provide a kit of the above-mentioned type which allows the successive implantation of a tubular endoprosthesis in a human blood vessel, then a prosthetic valve in the endoprosthesis so that the positioning of the prosthetic valve in the endoprosthesis is straightforward and secure.

To this end, the invention relates to a kit of the above-mentioned type, characterized in that at least one of the inner and outer surfaces has at least two portions having a variable cross-section along the longitudinal axis, the portions forming a proximal stop and a distal stop, respectively, to block the axial displacement of the outer surface along the inner surface in two opposing directions.

The kit according to the invention may comprise one or more of the following features, taken in isolation or according to any technically possible combination, the two portions having a variable cross-section over one of the surfaces form at least a fixing portion which protrudes radially, the fixing portion which protrudes radially being intended to be received in a corresponding hole which is provided in the other one of the surfaces, the other one of the surfaces has at least two portions having a variable cross-section along the longitudinal axis, the portions delimiting, in the other one of the surfaces, a housing for receiving the or each protruding portion, having a shape which complements that of the or each protruding portion, one of the surfaces delimits at least two protruding portions which are spaced-apart along the longitudinal axis, the or each protruding portion delimits two angular stop surfaces in order to block the rotation of the outer surface along the inner surface around the longitudinal axis, one of the surfaces delimits at least two protruding portions which are spaced-apart in an angular manner around the longitudinal axis, the inner surface has two portions which have a variable cross-section and which are connected to each other by means of a support portion which is radially recessed, the support portion having a length which is substantially equal to the length of the outer surface provided on the carrier reinforcement and delimiting, with the portions having a variable cross-section, a housing for receiving the carrier reinforcement, the two portions having a variable cross-section are delimited by two annular contractions which protrude in the channel and the portions having a variable cross-section are radio-opaque.

The invention also relates to a tubular endoprosthesis, of the type having an inner surface which delimits a channel having a longitudinal axis, characterized in that the inner surface has at least two portions which have a variable cross-section along the longitudinal axis, the portions forming a proximal stop and a distal stop, respectively, to block the axial displacement in two opposing directions of an outer surface provided on a prosthetic valve which is intended to be implanted on the inner surface in the channel.

Finally, the invention relates to a prosthetic valve which is intended to be implanted in a channel of a tubular endoprosthesis, comprising a carrier reinforcement which has an outer surface which is intended to be pressed against the inner surface of the endoprosthesis, the reinforcement being able to be radially deformed from a folded position for placement to a deployed position for implantation, a flexible shutter which is connected to the reinforcement and which can be deformed between a blocking position in which it is extended transversely and a release position in which it is contracted transversely under the action of the flow moving in the channel, characterized in that the outer surface of the carrier reinforcement has at least two portions having a variable cross-section along the longitudinal axis, the portions forming a proximal stop and a distal stop, respectively, to block the axial displacement of the valve relative to the tubular endoprosthesis.

BRIEF DESCRIPTION OF DRAWINGS

The invention will be better understood from a reading of the following description, given purely by way of example, and with reference to the appended drawings, in which.

DETAILED DESCRIPTION OF THE INVENTION

Figure 1:
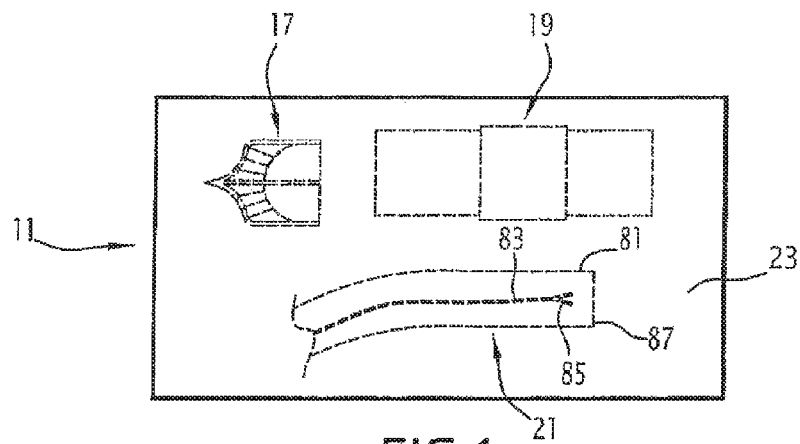
FIG. 1 is a plan view of a first kit according to the invention.
Figures 2, 3:
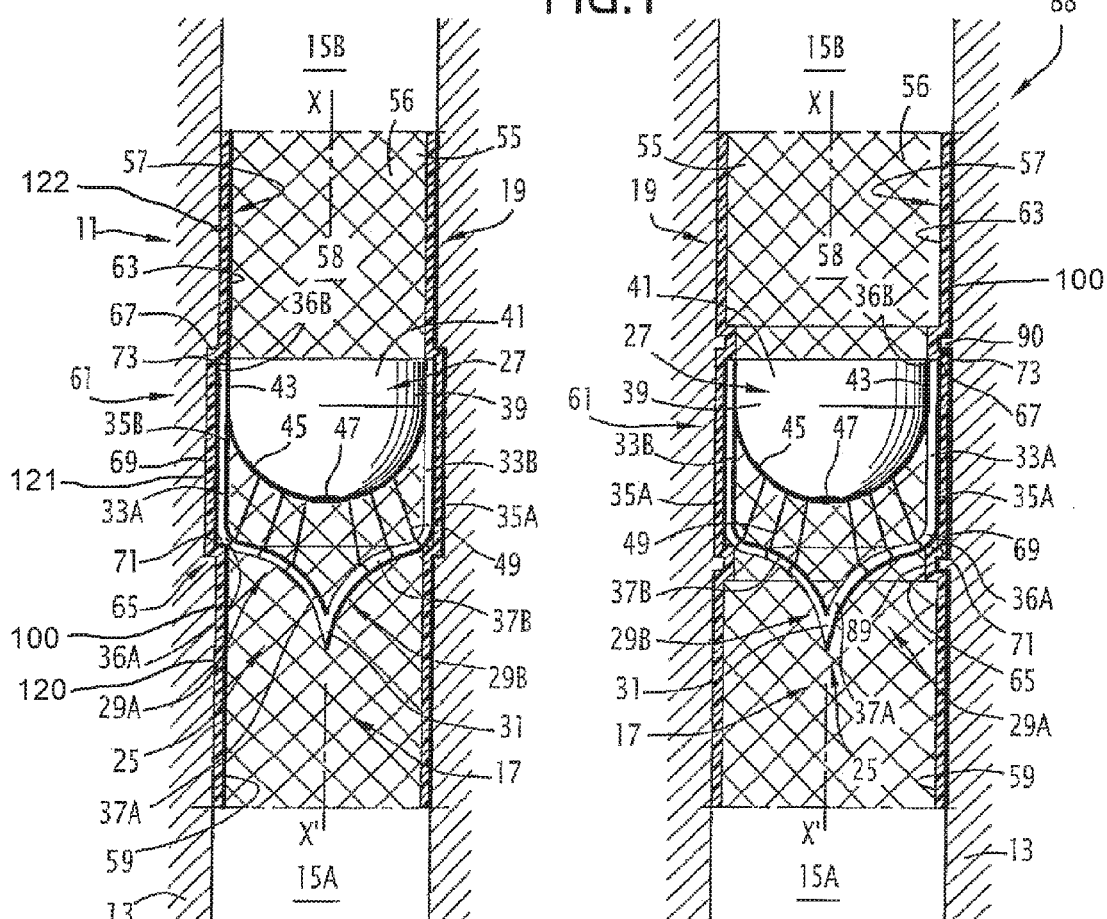
FIG. 2 is a cross-section of the first kit according to the invention implanted in a blood vessel.
FIG. 3 is a view similar to FIG. 2 of a second kit according to the invention.

A first kit according to the invention is illustrated in FIGS. 1 and 2.

FIG. 1 illustrates the kit 11 before it is implanted in a blood vessel, whilst FIG. 2 illustrates the kit 11 implanted in a blood vessel 13. The vessel 13 is, for example, a pulmonary artery which is connected, at the proximal end 15A thereof, to the outlet of the right ventricle of the heart, in particular of a human being and, at the distal end 15B thereof, to the lung.

As illustrated in FIG. 1, the kit 11 comprises a prosthetic valve 17, an endoprosthesis 19 which is intended to receive the prosthetic valve 17 and means 21 for implanting and removing the prosthetic valve 17 from the endoprosthesis 19.

The kit 11 is, for example, stored in a packaging 23.

As illustrated in FIG. 2, the interchangeable prosthetic valve 17 comprises a carrier reinforcement 25 and a deformable shutter 27 which is supported by the reinforcement 25 and which is fixedly joined thereto. The valve 17 generally has a longitudinal axis X-X'.

The carrier reinforcement 25 comprises integrated means for the centripetal compression thereof. More precisely, the reinforcement 25 is formed by at least two branches 29A, 29B and in particular three which are connected to each other at a first end 31 in order to form a pincer which is resiliently deformable between a deployed position in which the branches are remote from the centre axis X-X' and a folded position in which the two branches are close to the centre axis X-X'.

The two branches 29A, 29B are generally symmetrical relative to the centre axis X-X' which is aligned with the axis of the vessel, after implantation.

The length of the branches, measured along the axis X-X', is between 2 and 4 cm and is preferably equal to 3 cm.

Each branch 29A, 29B comprises a portion 33A, 33B for support on the endoprosthesis 19. Each support portion 33A, 33B is constituted by a rectilinear segment which generally extends along a generating line of the endoprosthesis 19 when the reinforcement 25 is deployed. Each support portion 33A, 33B has an outer surface 35A, 35B which is supported on the endoprosthesis 19.

The length of the support portions between a proximal edge 36A and a distal edge 36B is from 1 to 3 cm and is preferably approximately 2 cm.

These support portions 33A, 33B are extended by handling portions 37A, 37B which converge towards each other as far as the connection point 31. The handling portions are generally inclined relative to the centre axis X-X'.

The handling portions 37A, 37B are generally curved and have a centre of curvature which is arranged outside the space delimited between the two branches. In this manner, the portions 37A, 37B protrude towards the inner side of the pincer.

The shutter 27 is constituted by a flexible pocket 39 which has a distal opening 41 which is generally circular having an axis X-X', when the pocket 39 is inflated.

The pocket 39 has a generally cylindrical skirt 43 which is extended with a generally hemispherical base 45. The base 45 has a proximal hole 47 having a small diameter relative to the cross-section of the opening 41.

The pocket 39 is produced, for example, from polyurethane or from biological material (bovine pericardium).

The height of the skirt 43 is, for example, equal to 4 or 5 mm and is preferably between 2 and 5 mm.

The pocket 39 is connected to the support portions 33A, 33B by means of adhesive-bonding or any other appropriate means along the length of the generating lines of the skirt 43.

Advantageously, the pocket 39 is connected to the two branches 29A, 29B in such a manner that the two half-skirts delimited at one side and the other have lengths which are slightly different.

Finally, the base 45 is connected by means of filaments 49 to the handling portions 37A, 37B of the two branches of the carrier reinforcement in order to prevent the pocket being turned over by means of invagination.

Figure 4:
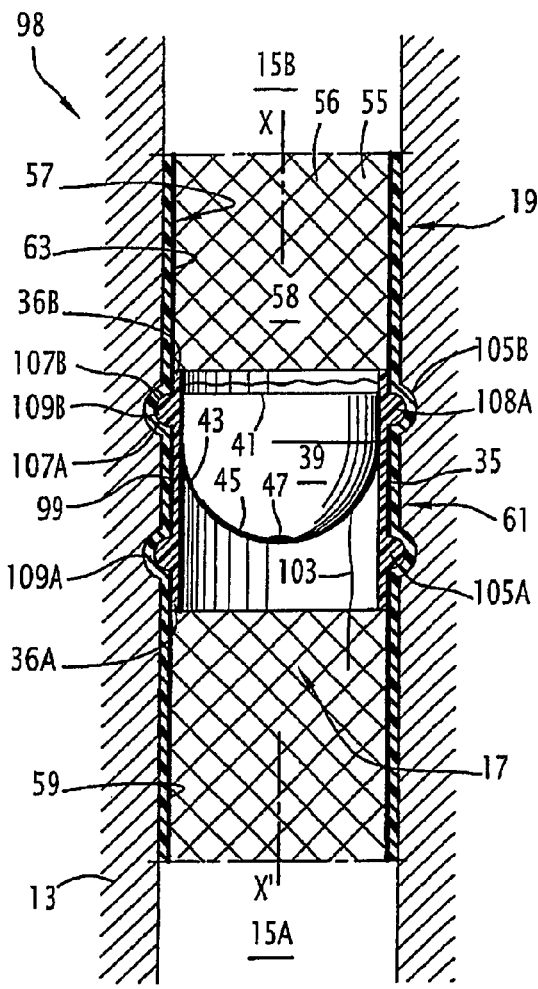
FIG. 4 is a view similar to FIG. 2 of a third kit according to the invention.

The endoprosthesis 19 is constituted, for example, by a tubular trellis 55 which is embedded in a film 56 which is extendable and liquid-tight, such as an elastomer material. The trellis 55 is constituted by stainless steel which has resilient properties, so that the endoprosthesis 19 is self-expandable. For example, as illustrated in FIGS. 2-4, the trellis is a stainless steel mesh embedded within an elastomer film. An endoprosthesis of this type is generally referred to as a "stent".

As known per se, the endoprosthesis is capable of changing shape spontaneously from a compressed state in which it has a small diameter to a dilated state in which it has a larger diameter, this dilated state constituting the rest state thereof.

In the implanted state thereof, as illustrated in FIG. 2, the endoprosthesis 19 is pressed, owing to its resilience, against the inner surface of the vessel 13, thus constituting a sheath inside the vessel 13.

The endoprosthesis 19 thus has an inner surface 57 which delimits a channel 58 for circulation of the blood flow, having an axis X-X'.

As illustrated in FIG. 2, the inner surface 57 of the endoprosthesis 19 comprises a proximal portion 59 which is substantially cylindrical, a hollow central portion 61 having a transverse dimension greater than the transverse dimensions of the proximal portion 59, and a distal portion 63 which is substantially cylindrical having a cross-section which is equal to the cross-section of the proximal portion 59. As also shown in FIG. 2, the corresponding outer surface 100 of the endoprosthesis 19 comprises a corresponding proximal portion 120, a central portion 121, and a distal portion 122.

The central portion 61 is delimited by a proximal shoulder portion 65 and a distal shoulder portion 67 which have a variable cross-section and which are connected to each other by means of an intermediate portion 69 having a constant (uniform) cross-section (diameter). The shoulder portion 65 is produced by means of an external radial deformation of the reinforcement 55. It has a cross-section which increases in a distal direction. The shoulder portion 65 forms a proximal stop 71 which is intended to co-operate with the proximal edge 36A of the support portions 33A, 33B.

The intermediate portion 69 has a cross-section which is substantially constant and greater than the cross-section of the proximal portion 59 and the distal portion 63. The length of the intermediate portion 69, taken along the axis X-X', is substantially equal to the length of the support portions 33A, 33B of the valve 17.

The distal shoulder portion 67 has a cross-section which decreases in a distal direction. It forms a distal stop 73 which is intended to co-operate with the distal edge 36B of the support portions 33A, 33B. As clearly shown in FIG. 2, each of the shoulder portions 65, 67 forms an edge against which the support portions 33A, 33B abut to prevent axial displacement of the support portions 33A, 33B.

The proximal shoulder portion 65 and the distal shoulder portion 67 are further covered with a radio-opaque material which facilitates the detection thereof using X-rays.

As illustrated in FIG. 1, the implantation and extraction means 21 comprise a catheter 81 having an inner cross-section which is less than the cross-section of the valve 17 in the deployed state thereof and having an outer cross-section which is less than the inner cross-section of the endoprosthesis 19.

The implantation and extraction means 21 also comprises a tool 83 for traction and thrust which is provided with a jaw 85 at the distal end thereof.

Before implanting the kit 11 according to the invention in the artery 13, the surgeon introduces in a known manner, the endoprosthesis 19 in the compressed state thereof as far as the implantation position thereof in the vessel 13. Then, the endoprosthesis 19 is placed in the dilated state thereof so that the reinforcement 25 is pressed against the vessel 13.

Then, the jaw 85 of the traction tool 83 grips the end 31 of the valve 17. The valve 17 is then inserted in the catheter 81 by means of traction on the tool 83.

The valve 17 is then in a retracted state. The catheter 81 is introduced into the vessel 13. It is moved as far as the inner channel 58 of the endoprosthesis 21 to a position substantially facing the proximal portion 59.

The support portions 33A, 33B of the valve 17 are extracted from the catheter and the valve 17 is deployed to the deployed state thereof for implantation. The valve 17 is pushed in a distal direction so that the distal edge 26B of the support portions is introduced into the hollow central portion 61 delimited in the inner surface 50 of the endoprosthesis 21.

When the distal edge 26B of each support portion 33A, 33B reaches the distal portion 67, it abuts the distal stop 73 which prevents the distal displacement thereof beyond this stop 73.

Furthermore, in this position, the proximal edge 26A of each support portion 33A, 33B is secured against the proximal stop 71, which prevents the proximal displacement thereof beyond this stop.

The valve 17 is therefore solidly fixed in the inner channel 50 of the endoprosthesis 21.

Furthermore, the relative position thereof with respect to the endoprosthesis 21 is determined in a precise manner by the dimensions of the hollow central portion 61.

An implanted prosthetic valve 17 of this type operates in the following manner. Following an expulsion of the right ventricle, when it increases in volume, the blood flow is drawn into the vessel 13 from the end 15B towards the end 15A. The blood fills the pocket 39 which presses on the endoprosthesis 14, as illustrated in FIG. 2, thus blocking the organic vessel 13 in a substantially sealed manner.

When the blood flows, the hole 47 allows a constant small flow of blood through the pocket 39, preventing the formation of a clot at the base of the pocket 39 owing to a possible stagnation of blood.

In contrast, during a contraction of the right ventricle, the blood flows from the end 15A towards the end 15B. The pocket 39 is then urged externally from the base 45, causing this pocket to become flattened. In this manner, the blood flow is free to circulate in the vessel 13 at one side and the other of the pocket 39.

After implanting a prosthesis of this type, the wall of the organic vessel 13 progressively adheres to the endoprosthesis 19. On the other hand, the endoprosthesis 19 constitutes a sheath which forms a screen between the prosthetic valve 17 and the wall of the organic vessel 13, thus preventing an agglomeration of the organic vessel 13 and the prosthetic valve 17. In this manner, it is possible to withdraw the prosthetic valve 17.

In particular, since the prosthetic valve 17 is provided with means for centripetal compression, it can be returned to the compressed state thereof and evacuated in a transluminal manner.

More precisely, in order to withdraw the prosthetic valve 17, the catheter 81 is introduced through the right auricle and the right ventricle and is arranged facing the end 31 of the carrier reinforcement which is in the form of a pincer.

The traction tool 83 is conveyed through the catheter 81. The jaw 85 grips the end 31 of the pincer. Whilst the open end, designated 87, of the catheter is in contact with the handling portions 37A, 37B, the carrier reinforcement is progressively pulled inside the catheter 81. By means of a cam effect, the two arms 29A, 29B are urged towards each other and the prosthetic valve is progressively moved into the state thereof in which it is urged and introduced into the catheter 81. The catheter 81 surrounding the prosthetic valve is then withdrawn from the human body.

A new catheter which contains a new prosthetic valve is then introduced into the human body and the valve is released by carrying out the operations set out above, in the reverse order.

In this second kit 88 according to the invention, illustrated in FIG. 3, the intermediate portion 69 has a cross-section which is substantially equal to the cross-section of the proximal portion 59 and the distal portion 63 of the inner surface 57.

The proximal and distal stops 71 and 73 are formed in the surface 67 on proximal and distal annular contractions 89 and 90 which protrude radially inside the channel 58 and form edges against which the support portions 33A, 33B abut to prevent axial movement.

The operation of this kit 88 is further substantially similar to that of the kit of FIG. 2.

In the third kit 98 according to the invention, illustrated in FIG. 4, the reinforcement of the valve 17 is formed by a resilient tubular metal trellis 99. The pocket 39 is connected along the open periphery thereof at two or three points to the tubular trellis 99.

The prosthetic valve 17 further comprises a constriction strand 103 which is permanently engaged in the different loops delimited by the trellis 99 along a circumference thereof. The strand 103 is closed in a loop. It is sufficiently long to allow the expansion of the valve 17. This strand 103 forms means for centripetal compression. The traction on this strand 103, for example, using a pincer brings about a constriction of the trellis 99 which allows the prosthetic valve 17 to be retracted after it has been engaged in a catheter 81.

Furthermore, the trellis 99 has, on the outer radial surface thereof, two annular strips 105A, 105B which are axially spaced-apart along the axis X-X'.

Each strip 105A, 105B extends in a transverse plane along the periphery of the outer surface of the trellis 99. Each strip 105A, 105B delimits an outer surface which has a portion 107A having a cross-section which increases in a distal direction along the axis X-X' and a portion 107B having a cross-section which decreases in a distal direction along the axis X-X'. The portions 107A, 107B form proximal and distal stops, respectively, for blocking the axial movement of the valve 17.

Furthermore, the endoprosthesis 21 comprises two annular recesses 109A, 109B which have shapes which substantially complement the annular strips 105A, 105B. Each recess 109A, 109B forms two front faces 108A and 108B which have a variable cross-section along the axis X-X' in the inner surface 57 of the endoprosthesis 21.

When the valve 17 is implanted in the endoprosthesis 21, the annular strips 105A, 105B are inserted in the corresponding recesses 109A, 109B. The stops 107A and 107B co-operate axially with the corresponding front faces 108A and 108B in order to prevent the axial displacement of the valve 17 relative to the endoprosthesis 21 in two opposing directions along the axis X-X'.

Figure 5:
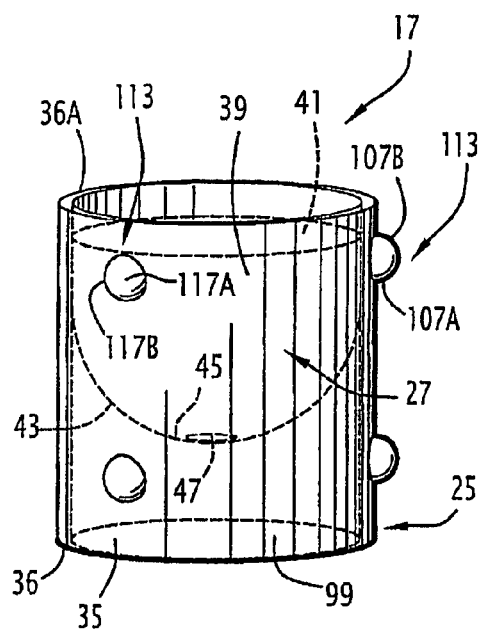
FIG. 5 is a perspective view of a valve of a fourth kit according to the invention.
Figure 6:
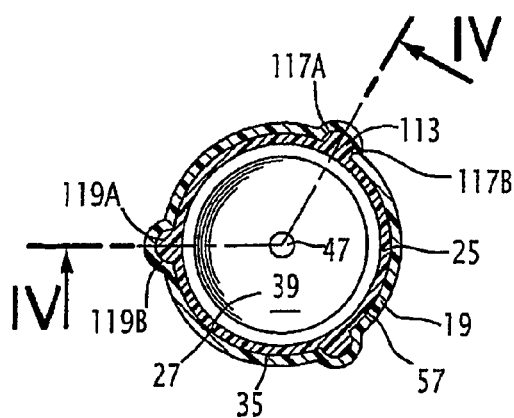
FIG. 6 is a section along a transverse plane of the fourth kit according to the invention, implanted in a blood vessel.

In the variant illustrated in FIGS. 5 and 6, the outer surface 35 of the valve 17 comprises a plurality of blocking pins 113 which protrude radially outwards. In this example, the blocking pins 113 are arranged in two transverse planes which are axially spaced-apart. Each transverse plane comprises three blocking pins 113 which are distributed angularly about the axis X-X'.

The inner surface 50 of the endoprosthesis 21 delimits recesses 115 having shapes which correspond to the blocking pins 113. As illustrated in FIG. 6, each blocking pin 113 delimits two angular stop surfaces 117A and 117B which co-operate with two corresponding angular stop front faces 119A, 119B which are delimited in the recesses 115.

In this manner, when the valve 17 is implanted in the endoprosthesis 21 and the pins 113 are inserted in the corresponding recesses 115, the valve 17 is axially blocked in terms of translation relative to the endoprosthesis 21 and blocked angularly around the axis X-X' relative to the endoprosthesis 21.

In a variant which is not illustrated, the pins 113 are inserted directly into the holes provided between the filaments of the reinforcement of the trellis 99. The endoprosthesis 19 has a cross-section which is substantially constant along the axis X-X'.

Owing to the invention which has been described above, it is therefore possible to provide an implantation kit which allows a prosthetic valve 17 to be fixed in a tubular endoprosthesis 21 in a precise, secure and removable manner using simple and cost-effective means.

The invention claimed is:

1. A kit to be implanted in a blood vessel, said kit comprising:
   a prosthetic valve including a carrier reinforcement; and
   a tubular endoprosthesis comprising an extendable tubular trellis, said endoprosthesis having:
      an outer surface with a proximal portion, a central portion, and a distal portion aligned along a longitudinal axis of said endoprosthesis, each of said proximal portion, said central portion, and said distal portion being cylindrical; and
      an inner surface delimiting a channel extending parallel to the longitudinal axis, said inner surface having at least two portions in which a cross-sectional area of said channel varies along the longitudinal axis at said at least two portions, said at least two portions forming a proximal stop and a distal stop, said at least two portions being connected to each other by a radially recessed central portion having a first length, and said central portion of said inner surface delimiting a housing with said at least two portions for receiving said carrier reinforcement of said prosthetic valve;
   wherein said prosthetic valve is to be implanted in said channel, and said prosthetic valve includes:
      said carrier reinforcement having an outer surface to be pressed against said inner surface of said endoprosthesis when implanted within said channel, said outer surface of said carrier reinforcement having a support portion with a second length substantially equal to said first length of said central portion of said inner surface, and said carrier reinforcement being radially deformable from a folded position for placement to a deployed position for implantation; and
      a flexible shutter connected to said carrier reinforcement and deformable between a blocking position, in which said flexible shutter is extended transversely, and a release position, in which said flexible shutter is contracted transversely due to flow moving through said channel; and
   wherein said endoprosthesis is configured so that, when said kit is assembled and said prosthetic valve is inserted into said endoprosthesis, said carrier reinforcement is received within said housing of said endoprosthesis so that axial displacement of said carrier reinforcement in two opposing axial directions beyond the proximal stop and the distal stop is prevented.

2. The kit according to claim 1, wherein each of said at least two portions is an annular contraction protruding into said channel.

3. The kit according to claim 1, wherein said at least two portions are radio-opaque.

4. The kit according to claim 1, wherein each of said at least two portions is formed as a shoulder portion.

5. The kit according to claim 4, wherein said at least two portions comprise a first shoulder portion and a second shoulder portion, wherein an intermediate portion of said endoprosthesis is located between said first shoulder portion and said second shoulder portion and has a uniform cross section along an axial direction thereof, said prosthetic valve to be arranged within said intermediate portion.

6. The kit according to claim 4, wherein said at least two portions comprise a first shoulder portion and a second shoulder portion, wherein each of said first shoulder portion and said second shoulder portion has an edge forming a respective one of said proximal stop and said distal stop, and against which said support portion abuts so as to prevent axial displacement of said support portion and said carrier reinforcement.

7. The kit according to claim 1, wherein each of said at least two portions has an edge forming a respective one of said proximal stop and said distal stop, and against which said support portion abuts so as to prevent axial displacement of said support portion and said carrier reinforcement.

* * * * *